(12) United States Patent
Al-Ali

(10) Patent No.: US 7,880,606 B2
(45) Date of Patent: Feb. 1, 2011

(54) PHYSIOLOGICAL TREND MONITOR

(75) Inventor: Ammar Al-Ali, Tustin, CA (US)

(73) Assignee: Masimo Corporation, Irvine, CA (US)

( * ) Notice: Subject to any disclaimer, the term of this patent is extended or adjusted under 35 U.S.C. 154(b) by 207 days.

(21) Appl. No.: 12/070,061

(22) Filed: Feb. 12, 2008

(65) Prior Publication Data

US 2008/0228052 A1  Sep. 18, 2008

Related U.S. Application Data

(63) Continuation of application No. 11/717,591, filed on Mar. 13, 2007, now Pat. No. 7,355,512, which is a continuation of application No. 11/405,815, filed on Apr. 18, 2006, now Pat. No. 7,190,261, which is a continuation of application No. 10/975,860, filed on Oct. 28, 2004, now Pat. No. 7,030,749, which is a continuation of application No. 10/351,735, filed on Jan. 24, 2003, now Pat. No. 6,822,564.

(60) Provisional application No. 60/351,510, filed on Jan. 24, 2002.

(51) Int. Cl.
*G08B 29/00* (2006.01)

(52) U.S. Cl. ............... 340/511; 340/539.12; 600/322

(58) Field of Classification Search ............... 340/511, 340/539.12, 573.1; 600/322, 323
See application file for complete search history.

(56) References Cited

U.S. PATENT DOCUMENTS

| | | | |
|---|---|---|---|
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |

(Continued)

*Primary Examiner*—John A Tweel, Jr.
(74) *Attorney, Agent, or Firm*—Knobbe, Martens, Olson & Bear LLP

(57) ABSTRACT

A physiological trend monitor has a sensor signal responsive to multiple wavelengths of light transmitted into a tissue site. The transmitted light is detected after attenuation by pulsatile blood flow within the tissue site. A processor has an input responsive to the sensor signal and a physiological parameter output. Features are extracted from the physiological parameter output. Criteria are applied to the features. An alarm output is generated when the criteria are satisfied.

15 Claims, 9 Drawing Sheets

U.S. PATENT DOCUMENTS

| | | |
|---|---|---|
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,321,100 B1 | 11/2001 | Parker |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-All |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |

| | | |
|---|---|---|
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |

PHYSIOLOGICAL TREND MONITOR

CROSS-REFERENCE TO RELATED APPLICATIONS

This application is a CON of Ser. No. 11/717,591 filed Mar. 13, 2007 now U.S. Pat. No. 7,355,512, which is a CON of Ser. No. 11/405,815 filed Apr. 18, 2006 now U.S. Pat. No. 7,190, 261, which is a CON of Ser. No. 10/975,860 filed Oct. 28, 2004 now U.S. Pat. No. 7,030,749, which is a CON of Ser. No. 10/351,735 filed Jan. 24, 2003 now U.S. Pat. No. 6,822, 564, which claims the benefit of Ser. No. 60/351,510 filed Jan. 24, 2002. All patents, patent applications and provisional patent applications cited above are incorporated by reference herein.

BACKGROUND OF THE INVENTION

Physiological measurement instruments employed in healthcare environments often feature visual and audible alarm mechanisms that alert a caregiver when a patient's vital signs are outside of predetermined limits. One example is a pulse oximeter, which measures the oxygen saturation level of arterial blood, an indicator of oxygen supply. A typical pulse oximeter displays a numerical readout of the patient's oxygen saturation, a numerical readout of pulse rate, and a plethysmograph, which is indicative of a patient's pulse. In addition, a pulse oximeter provides an alarm that warns of a potential desaturation event.

FIG. 1 illustrates a prior art pulse oximeter portion 100 having a signal input 101 and generating an oxygen saturation measurement output 103 and an alarm output 105. The pulse oximeter portion 100 has an oxygen saturation ($SpO_2$) processor 110 and an associated threshold detector 120. The $SpO_2$ processor 110 derives an oxygen saturation measurement from the signal input 101. The signal input 101 is typically an amplified, filtered, digitized and demodulated sensor signal. A sensor emits both red and infrared (IR) wavelength light, which is transmitted through a patient's tissue, detected and input to the pulse oximeter. The pulse oximeter calculates a normalized ratio (AC/DC) of the detected red and infrared intensities, and an arterial oxygen saturation value is empirically determined based on a ratio of these normalized ratios, as is well-known in the art. The oxygen saturation measurement output 103 is typically a digital signal that is then communicated to a display.

FIG. 2 illustrates the operation of a conventional threshold detector 120 (FIG. 1) utilizing a graph 200 of oxygen saturation 201 versus time 202. The graph 200 displays a particular oxygen saturation measurement 210 corresponding to the measurement output 103 (FIG. 1) and a predetermined alarm threshold 206. During an alarm time period 270 when the measured oxygen saturation 210 is below the threshold 206, an alarm output 105 (FIG. 1) is generated, which triggers a caregiver alert. Adjusting the threshold 206 to a lower value of oxygen saturation 201 reduces the probability of an alarm, i.e. reduces the probability of a false alarm and increases the probability of a missed event. Likewise, adjusting the threshold 206 to a higher value of oxygen saturation 201 increases the probability of an alarm, i.e. increases the probability of a false alarm and decreases the probability of a missed event.

SUMMARY OF THE INVENTION

One aspect of a physiological trend monitor comprises transmitting light into a patient tissue site, generating a sensor signal, detecting a blood parameter trend according to the sensor signal and generating an alarm according to the blood parameter trend. The transmitted light has multiple wavelengths. The sensor signal is responsive to the light after attenuation by pulsatile arterial blood flow within the tissue site. In various embodiments, the detecting comprises deriving a curve-fitting blood parameter measurement. A blood parameter slope is calculated from the blood parameter measurement. The alarm is responsive to a negative value of the blood parameter slope. A smoothed blood parameter measurement is derived. A threshold value is set for the smoothed blood parameter measurement. The alarm is responsive to the smoothed blood parameter measurement crossing the threshold value.

Another aspect of a physiological trend monitor comprises a sensor signal responsive to multiple wavelengths of light transmitted into a tissue site and detected after attenuation by pulsatile blood flow within the tissue site. A processor has an input responsive to the sensor signal and a physiological parameter output. Features are extracted from the physiological parameter output. Criteria are applied to the features. An alarm output is generated when the criteria are satisfied. In various embodiments a pattern memory stores feature values and a comparator compares the features with the stored feature values. The criteria determine a match between the features and the stored feature values so as to trigger the alarm output. At least one of the features relate to the number of threshold crossings over a specified time period. At least one of the features relate to a duration of a threshold crossing by the physiological parameter output. At least one of the features relate to a trend in the physiological parameter and a slope of that trend over a specified time period.

A further aspect of a physiological trend monitor comprises a detector responsive to multiple wavelengths of light transmitted into a tissue site after attenuation by pulsatile blood flow within the tissue site so as to generate a sensor signal. A processor means calculates a physiological measurement in response to the sensor signal. A pattern extractor means identifies features of the physiological measurement. A pattern memory means stores a reference pattern. A pattern comparator means triggers an alarm if the identified features match the reference pattern. In various embodiments, a threshold is input to the pattern extractor. The identified features comprise at least the number of times the physiological measurement crosses the threshold within a predetermined time period. The identified features comprise at least the duration of each time the physiological measurement crosses the threshold. The physiological measurement comprises a predictive oxygen saturation measurement. A second processor means calculates an integrator oxygen saturation measurement.

DETAILED DESCRIPTION OF THE PREFERRED EMBODIMENTS

Figure 3:
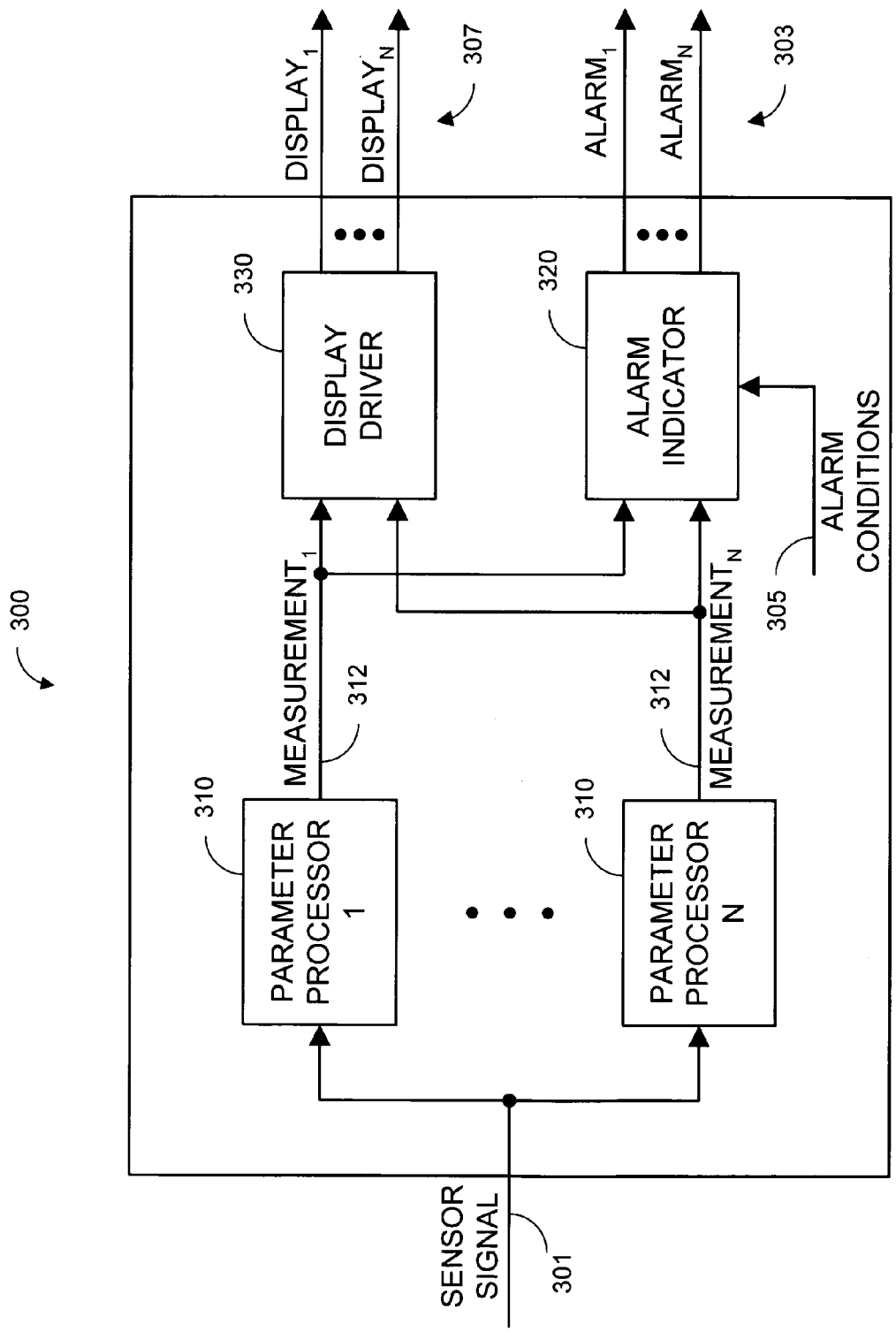
FIG. 3 is a block diagram of an alarm processor utilizing parallel measurements of a physiological parameter.

FIG. 3 illustrates a parallel measurement alarm processor 300. The alarm processor 300 has a sensor signal input 301 responsive to a physiological parameter and provides one or more alarm outputs 303 to indicate that the physiological parameter may have exceeded particular limits. The alarm processor 300 also has multiple parameter processors 310, which do not necessarily have the same or similar internal configurations. The multiple parameter processors 310 input the sensor signal 301 and provide parallel measurements 312 of the physiological parameter, each measurement having differing characteristics, such as response time or bandwidth to name a few. The alarm processor 300 further has an alarm indicator 320 that inputs the parallel parameter measurements 312 and generates the alarm outputs 303 based upon alarm conditions 305. The alarm outputs 303 change state to indicate that the parameter may have exceed one or more limits and to trigger an alarm accordingly. The alarm conditions 305 define particular limits with respect to one or more of the measurements 312. The alarm conditions 305 may be predefined, such as by user input, or determined by a separate process, such as a measurement of sensor signal quality or data confidence as described in U.S. patent application Ser. No. 09/858,114 entitled "Pulse Oximetry Data Confidence Indicator," assigned to Masimo Corporation, Irvine, Calif. and incorporated by reference herein. The alarm processor 300 may also have a display driver 330 that processes one or more of the parameter measurements 312 and provides one or more display outputs 307.

Figure 1:
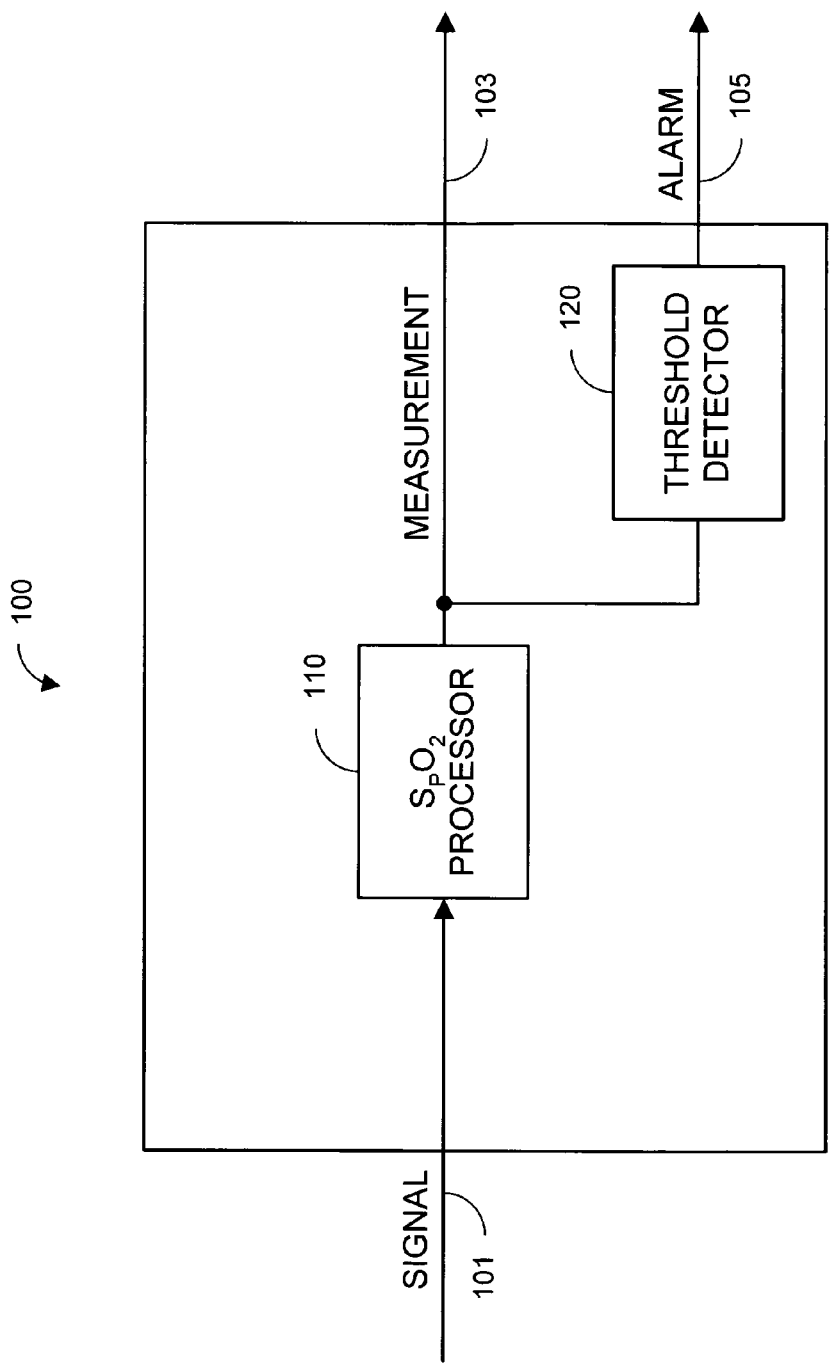
FIG. 1 is a block diagram of a prior art pulse oximeter portion.
Figure 2:
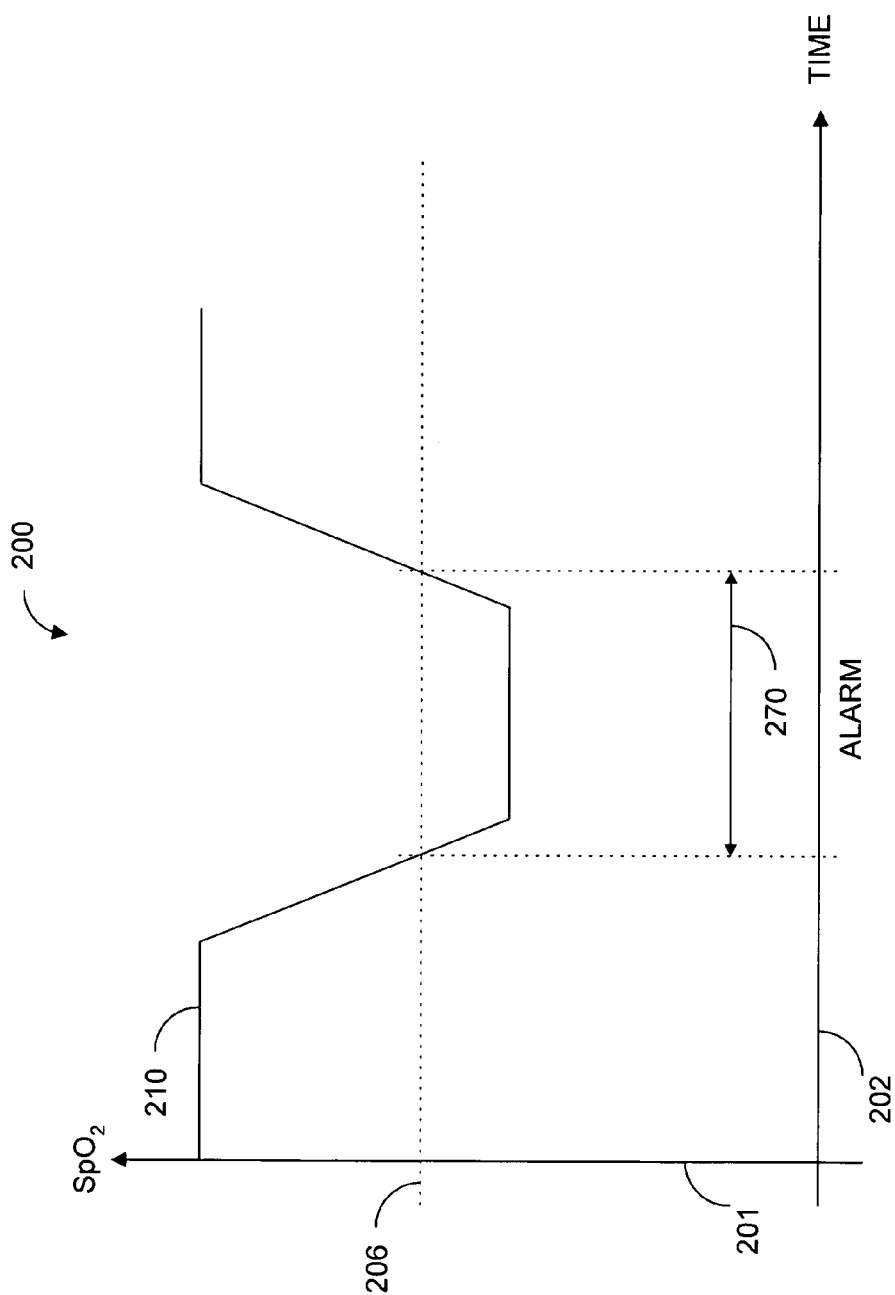
FIG. 2 is a graph of oxygen saturation versus time illustrating a conventional threshold detector alarm.
Figure 4:
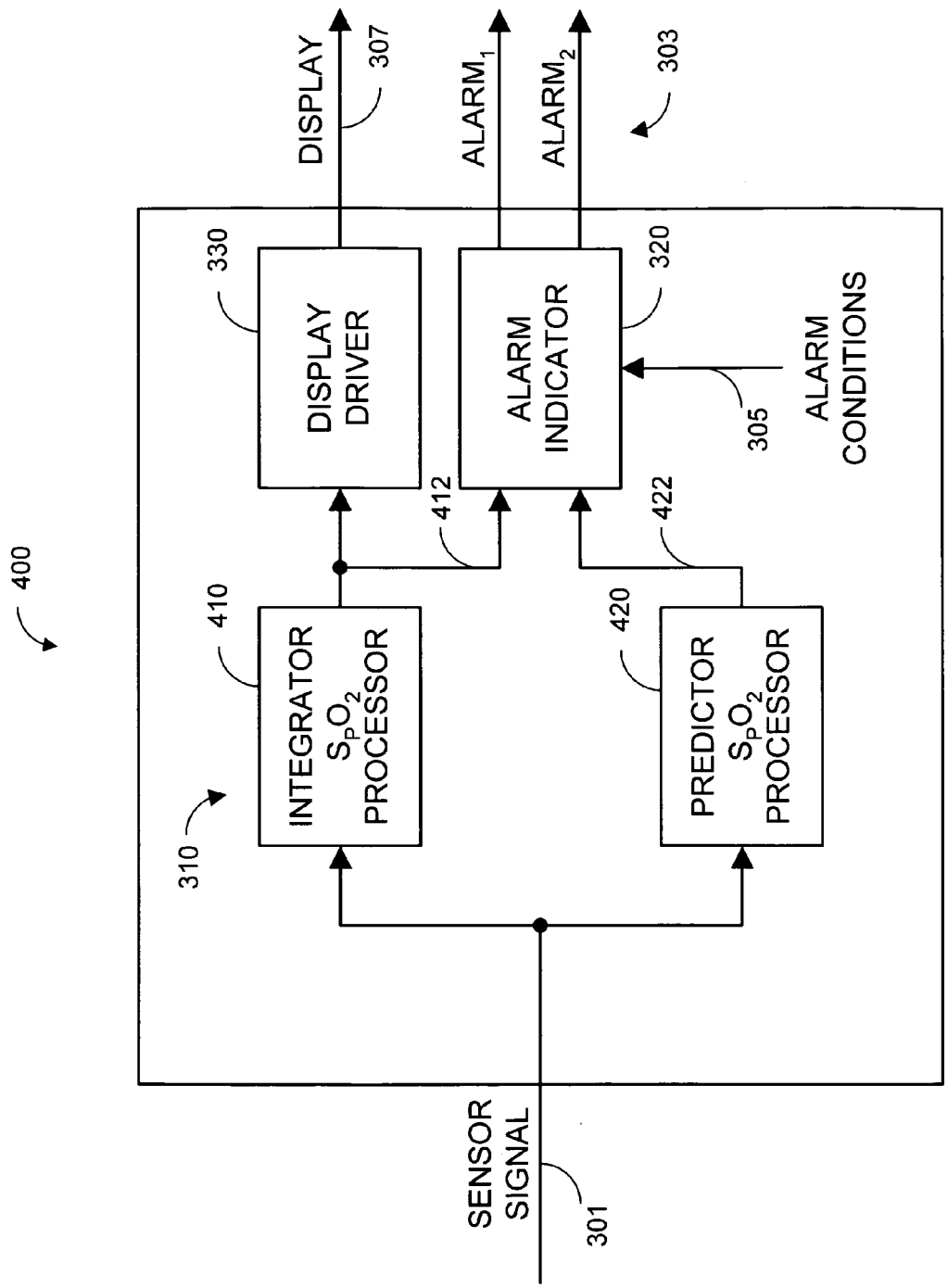
FIG. 4 is a block diagram of a pulse oximeter processor utilizing dual oxygen saturation measurements.

FIG. 4 illustrates a pulse oximeter embodiment 400 of the alarm processor 300 (FIG. 3) described above. A pulse oximeter sensor (not shown) provides a signal input 301 that is responsive to arterial oxygen saturation, as described with respect to FIG. 1, above. The alarm processor 400 has dual oxygen saturation processors 310. An integrator oxygen saturation ($SpO_2$) processor 410 outputs a slow $SpO_2$ measurement 412, i.e. a measurement having a slow response time to changes in the $SpO_2$ parameter. A predictor $SpO_2$ processor 420 outputs a fast $SpO_2$ measurement 422, i.e. a measurement having a fast response time that tracks changes in the $SpO_2$ parameter. The slow $SpO_2$ measurement 412 is input to a display driver 330, which provides an oxygen saturation display output 307. For example, the display output 307 may be input to a digital display that provides a numerical readout of oxygen saturation to a caregiver. Both the slow $SpO_2$ measurement 412 and the fast $SpO_2$ measurement 422 are input to an alarm indicator 320 that generates at least one alarm output 303 based upon alarm conditions 305, as described in further detail with respect to FIGS. 5-8, below.

The integrator $SpO_2$ processor 410, advantageously, provides a smoothed measurement of oxygen saturation suitable for threshold detection. The predictor $SpO_2$ processor 420, advantageously, provides a curve-fitting or a predictive measurement of oxygen saturation that detects trends in oxygen saturation, as described in further detail with respect to FIG. 5 and FIGS. 6A-B, below. Further, the predictor $SpO_2$ processor 420 advantageously tracks oxygen saturation details that may signal a critical physiological event, as described in further detail with respect to FIGS. 7-8, below. The integrator $SpO_2$ processor 410 and predictor $SpO_2$ processor 420 may be a pulse oximeter as described in U.S. patent application Ser. No. 09/586,845 entitled "Variable Mode Averager," assigned to Masimo Corporation, Irvine, Calif. and incorporated by reference herein.

Figure 5:
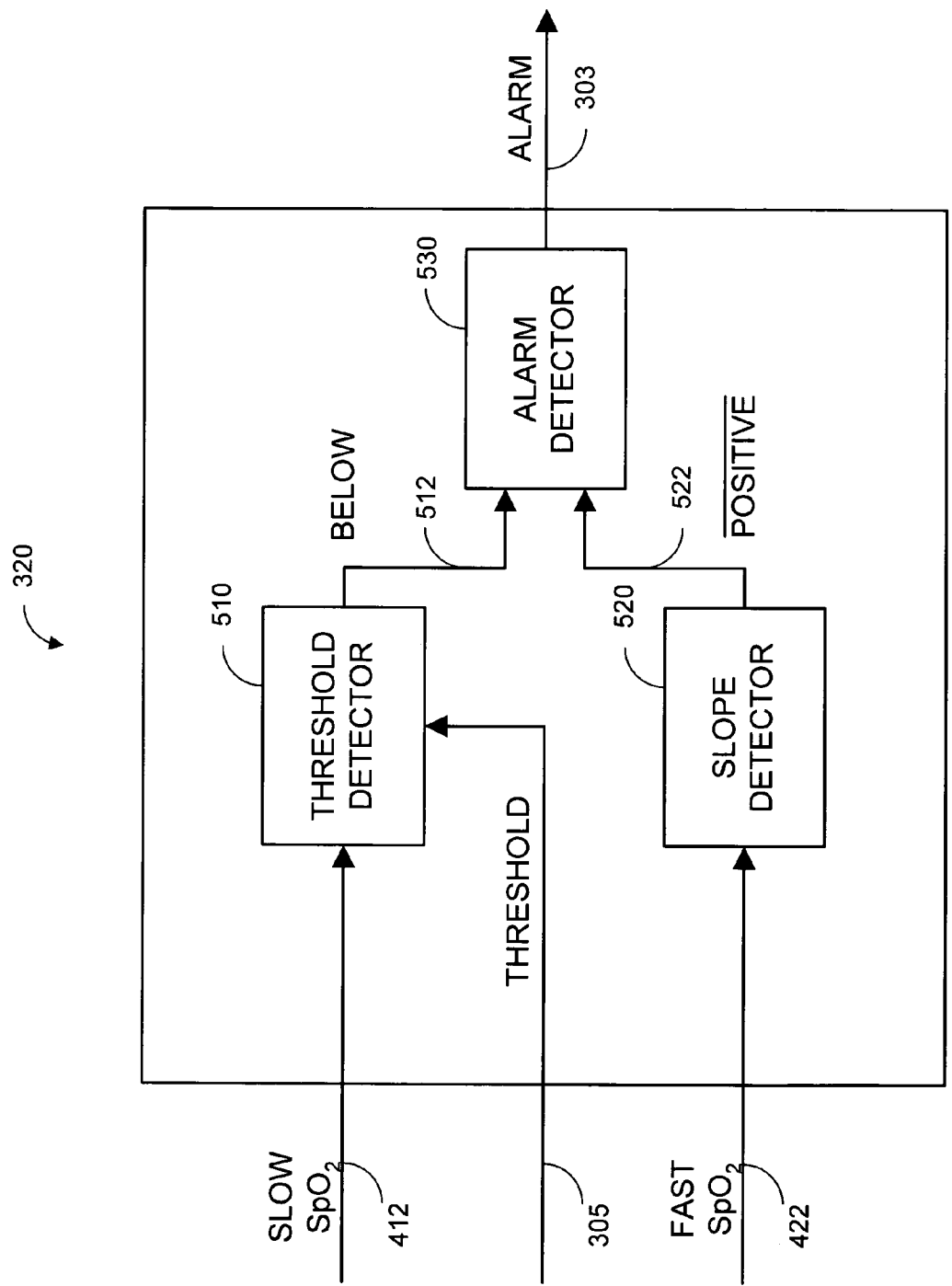
FIG. 5 is a block diagram of a predictive alarm indicator utilizing a threshold detector with a slow oxygen saturation measurement input and a slope detector with a fast oxygen saturation measurement input.

FIG. 5 illustrates a trend embodiment of an alarm indicator 320, which has a threshold detector 510, a slope detector 520 and alarm detector 530. The threshold detector 510 has a slow $SpO_2$ measurement 412 and a threshold alarm condition 305 as inputs and a logic output BELOW 512. The slope detector 520 has a fast $SpO_2$ measurement 422 input and a logic output POSITIVE/522. The alarm detector 530 has BELOW 512 and POSITIVE/522 logic inputs and generates an alarm output 303. The threshold detector 510 is a comparator that asserts BELOW 512 while the slow $SpO_2$ measurement 412 is less in value than the value of the threshold 305. The slope detector 520 is a differentiator and comparator that asserts POSITIVE/ 522 while the slope of the fast $SpO_2$ measurement 422 is non-positive, i.e. while the derivative of the fast $SpO_2$ measurement 422 is zero or less than zero. The alarm detector 530 performs a logical AND function, asserts the alarm output 303 and indicates an alarm when BELOW 512 and POSITIVE/522 are both asserted. In this manner, an alarm output 303 only changes state when the slow $SpO_2$ measurement 412 is below a threshold 305 and the fast $SpO_2$ measurement 422 has not begun to increase in value. Advantageously, the trend recognition alarm indicator 320 reduces false alarms by suppressing a threshold-based alarm on the slow $SpO_2$ measurement 412 when the fast $SpO_2$ measurement 422 determines that a patient's oxygen saturation is in recovery, as described in further detail with respect to FIGS. 6A-B, below.

Figure 6A:
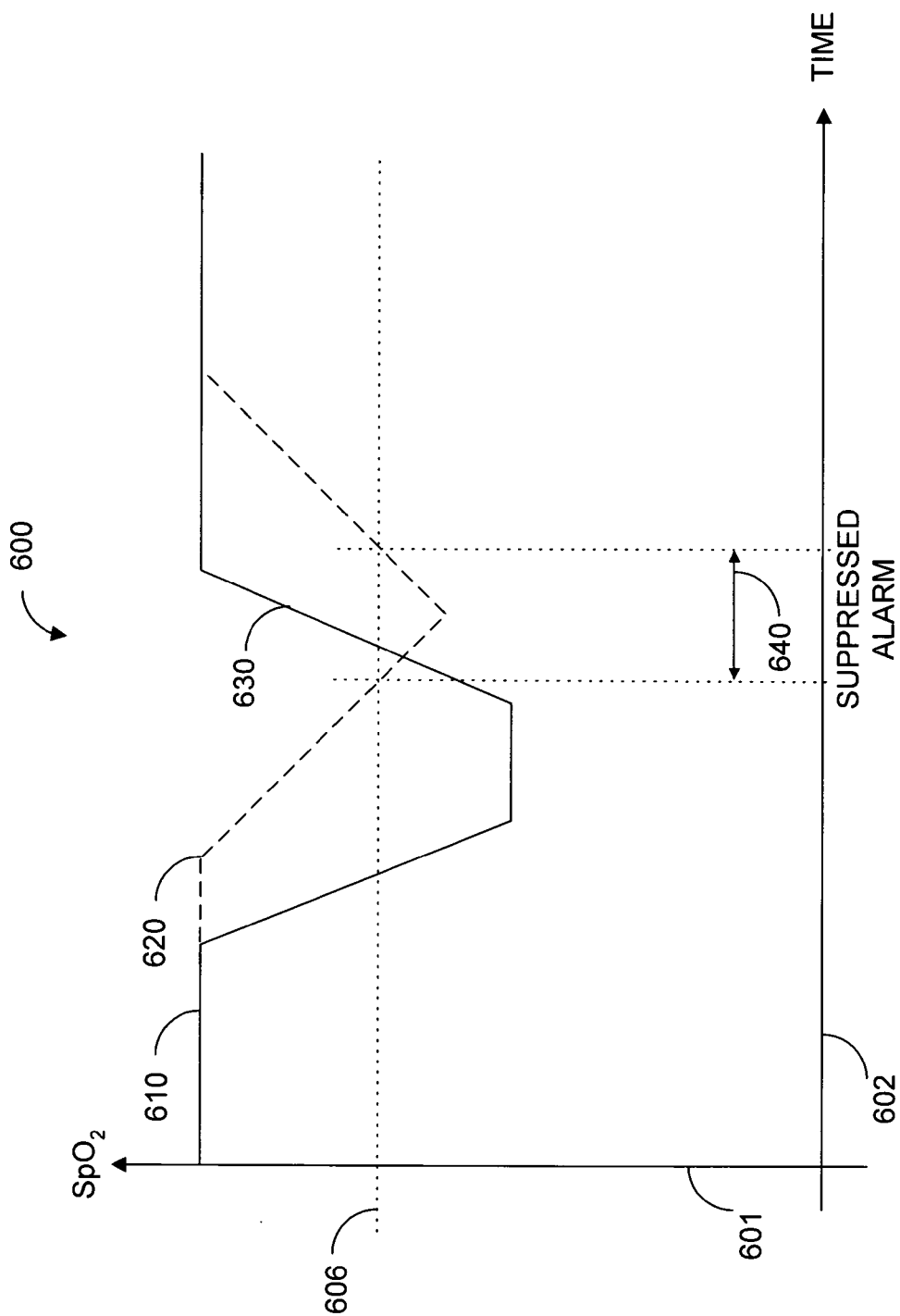
FIGS. 6A-B are graphs of oxygen saturation versus time illustrating operation of the alarm indicator according to FIG. 5.
Figure 6B:
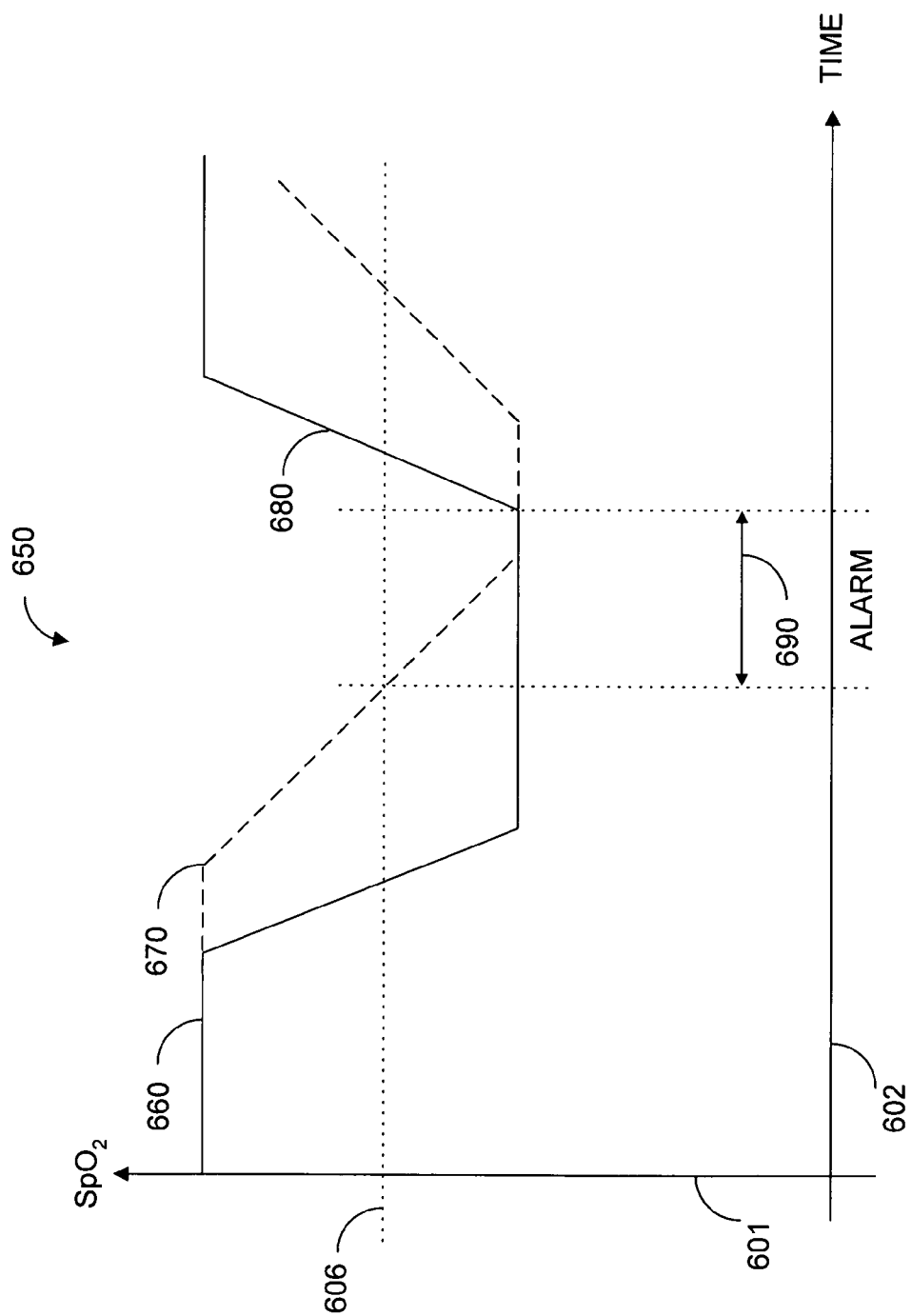

FIGS. 6A-B illustrate operation of the trend recognition alarm indicator 320 (FIG. 5). In FIG. 6A, a graph 600 has an $SpO_2$ axis 601 and a time axis 602. Shown along the $SpO_2$ axis 601 is a constant $SpO_2$ value 606 corresponding to a threshold 305 (FIG. 5). The graph 600 shows a first plot of $SpO_2$ versus time 610 corresponding to a fast $SpO_2$ measurement 422 (FIG. 5). The graph 600 also shows a second plot of $SpO_2$ versus time 620 corresponding to a slow $SpO_2$ measurement 412 (FIG. 5). A suppressed alarm interval 640 along the time axis 602 corresponds to an alarm that would be indicated by the threshold detector 510 (FIG. 5) but is suppressed as occurring during a positive slope portion 630 of a fast $SpO_2$ measurement 610. The alarm detector 530 (FIG. 5) would not assert an alarm output 303 (FIG. 5) during this interval.

In FIG. 6B, a graph 650 shows a first plot of $SpO_2$ versus time 660 corresponding to a fast $SpO_2$ measurement 422 (FIG. 5). The graph 650 also shows a second plot of $SpO_2$ versus time 670 corresponding to a slow $SpO_2$ measurement 412 (FIG. 5). An alarm interval 690 along the time axis 602 corresponds to an alarm period triggered by the alarm output 303 (FIG. 5). This alarm interval 640 occurs while a slow $SpO_2$ measurement 670 is below the threshold 606 and before a positive slope portion 680 of a fast $SpO_2$ measurement 660.

Figure 7:
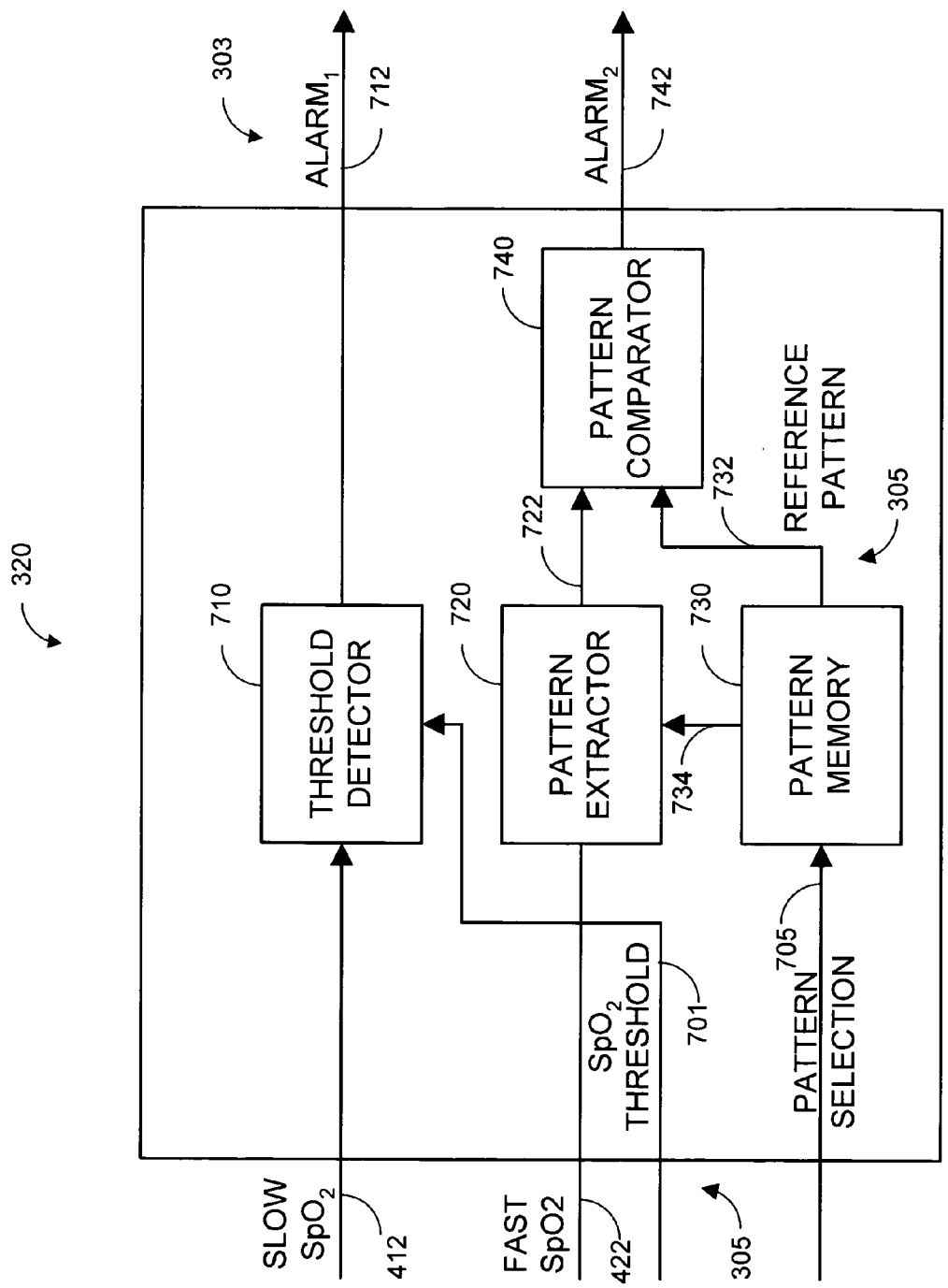
FIG. 7 is a block diagram of a pattern recognition alarm indicator utilizing a threshold detector with a slow oxygen saturation measurement input and a pattern extractor with a fast oxygen saturation measurement input.

FIG. 7 illustrates a pattern recognition embodiment of an alarm indicator 320, having a threshold detector 710, a pattern extractor 720, a pattern memory 730 and a pattern comparator 740. Further, the alarm indicator 320 has slow $SpO_2$ 412 and fast $SpO_2$ 422 measurement inputs in addition to threshold 701 and reference pattern 732 alarm condition inputs 305. The threshold detector 710 has a slow $SpO_2$ measurement 412 and a $SpO_2$ threshold 701 as inputs and a first alarm output 712. The threshold detector 710 changes the state of the first alarm output 712 when the value of the slow SpO$_2$ measurement 412 crosses the SpO$_2$ threshold 701. For example, the first alarm output 712 changes state to trigger an alarm when the slow SpO$_2$ measurement 412 becomes less than the SpO$_2$ threshold 701.

As shown in FIG. 7, the pattern extractor 720 has a fast SpO$_2$ measurement 422 and a pattern threshold 734 as inputs and an extracted pattern output 722. The pattern extractor 720 identifies features of the fast SpO$_2$ measurement 422 that may be used for pattern matching. Features may be, for example, the number of times the fast SpO$_2$ measurement 422 crosses the pattern threshold 734 within a certain time period, or the duration of each time period that the fast SpO$_2$ measurement 422 is less than the pattern threshold 734, to name a few. The pattern memory 730 has a pattern selection input 705 and a reference pattern output 732. The pattern memory 730 stores values for particular features that are identified by the pattern extractor 720. The reference pattern output 732 transfers these stored values to the pattern comparator 740. The pattern memory 730 may be nonvolatile and one or more patterns may be stored at the time of manufacture or downloaded subsequently via a data input (not shown). One of multiple patterns may be determined via the pattern selection input 705, by a user or by a separate process, for example. The pattern threshold 734 may be generated in response to the pattern selection input 705 or in conjunction with a selected reference pattern 732.

Also shown in FIG. 7, the pattern comparator 740 has the extracted pattern 722 and the reference pattern 732 as inputs and generates a second alarm output 742. That is, the pattern comparator 740 matches extracted measurement features provided by the pattern extractor 720 with selected features retrieved from pattern memory 730, changing the state of the second alarm output 742 accordingly. For example, the second alarm output 742 changes state to trigger an alarm when features of the fast SpO$_2$ measurement 422 match the reference pattern output 732. Advantageously, the pattern recognition alarm indicator 320 reduces missed events by supplementing the threshold-based first alarm output 712 responsive to the slow SpO$_2$ measurement 412 with a pattern-based second alarm output 742 responsive to detail in the fast SpO$_2$ measurement 422. In this manner, if a patient's oxygen saturation is, for example, irregular or intermittent, the second alarm output 742 may trigger a caregiver alert when the first alarm output 712 does not, as described in further detail with respect to FIG. 8, below.

Figure 8:
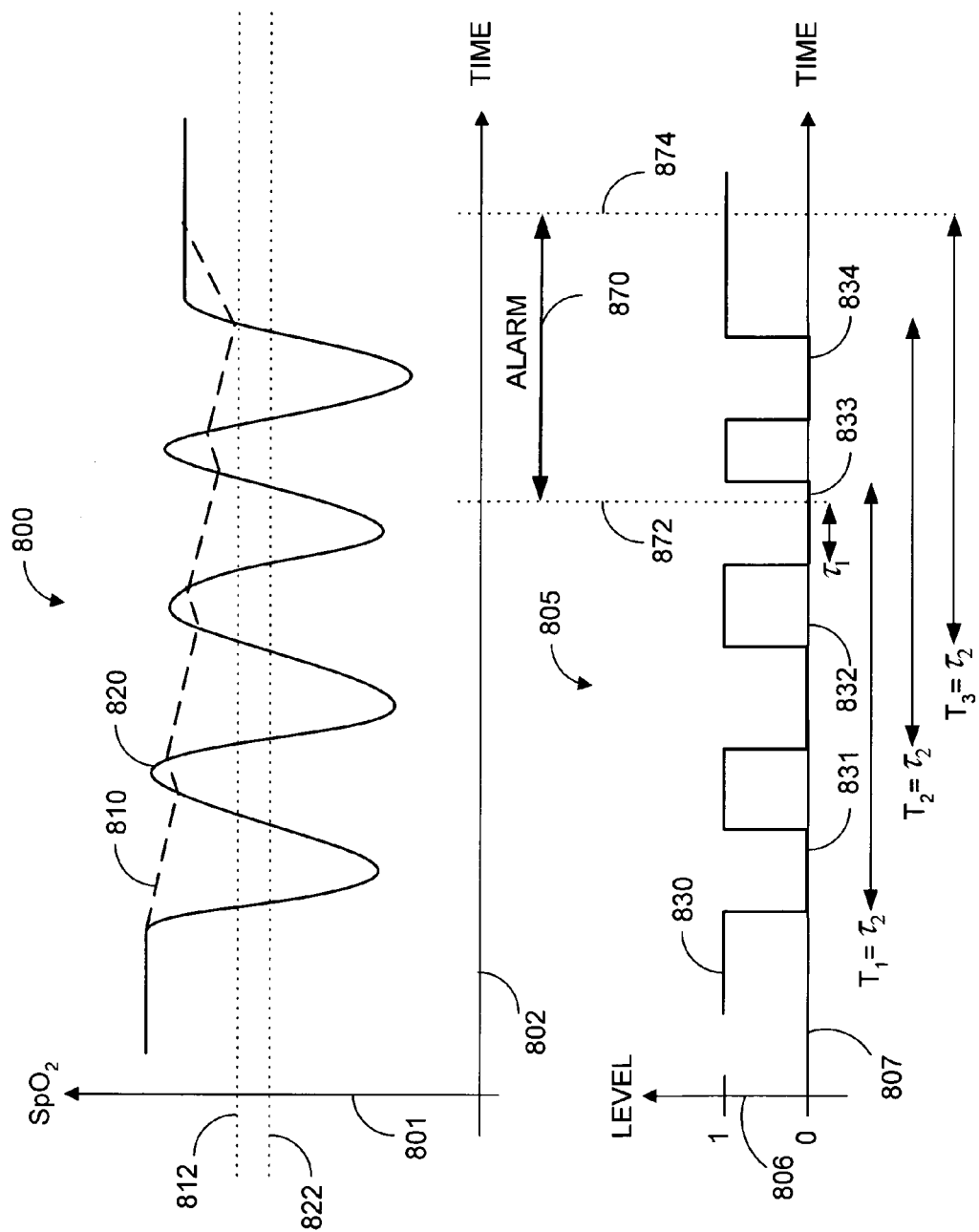
FIG. 8 is a graph of oxygen saturation versus time illustrating the pattern recognition alarm indicator according to FIG. 7.

FIG. 8 illustrates operation of a pattern recognition alarm indicator 320 (FIG. 7), as described above. A graph 800 has a SpO$_2$ axis 801 and a time axis 802. The graph 800 shows a SpO$_2$ plot versus time 810 corresponding to the slow SpO$_2$ measurement 412 (FIG. 7). Shown along the time axis 802 is a constant SpO$_2$ value 812 corresponding to the SpO$_2$ threshold 701 (FIG. 7). Due to the short duration of irregular and intermittent drops in SpO$_2$, the slow SpO$_2$ measurement 810 does not fall below the SpO$_2$ threshold 812. Thus, the first alarm output 712 (FIG. 7) does not trigger an alarm in this example.

Also shown in FIG. 8, the graph 800 shows a SpO$_2$ plot versus time 820 corresponding to the fast SpO$_2$ measurement 422 (FIG. 7). Shown along the time axis 802 is a constant SpO$_2$ value 822 corresponding to the pattern threshold 734 (FIG. 7). A corresponding graph 805 has a logic level axis 806 and a time axis 807. The graph 805 shows a logic level plot versus time 830 corresponding to the extracted pattern output 722 (FIG. 7). The logic level plot 830 has a "1" level when the fast SpO$_2$ plot 820 is above the pattern threshold 822 and a "0" level when the fast SpO$_2$ plot 820 is below the pattern threshold 822. In this manner, the logic level plot 830 indicates the number and duration of times the fast SpO$_2$ plot 820 falls below a threshold value 822.

Further shown in FIG. 8, an alarm interval 870 along the time axis 802 corresponds to an alarm period indicated by the pattern comparator 740 (FIG. 7). This alarm interval 870 occurs after a reference pattern 732 (FIG. 7) is detected as matching an extracted pattern 722 (FIG. 7) and ends, correspondingly, when there is no longer a match. For example, assume that the reference pattern output 732 (FIG. 7) has the alarm criteria that at least three below threshold periods of minimum duration $T_1$ must occur during a maximum period $T_2$, where the value of $T_1$ and $T_2$ are illustrated along the time axis 807. The below threshold time periods 831-834 are each greater in duration than $T_2$ and a first set of three, below-threshold time periods 831-833 occurs within a time period $T_1=T_2$, as illustrated. Thus, the alarm interval beginning 872 is triggered by the second alarm output 742 (FIG. 7). A second set of three, below-threshold time periods 832-834 also occurs within a time period $T_2=T_2$, as illustrated. Thus, the alarm interval 870 continues. There is no third set of three, below-threshold time periods. Thus, after the end of the time interval $T_3=T_2$, the alarm interval end 874 is triggered. This example illustrates how the pattern recognition alarm indicator 320 (FIG. 7) can trigger an alarm on an event, such as a period of irregular heartbeats, that might be missed by a threshold-based alarm responsive to the slow SpO$_2$ measurement 412.

Although some alarm processor embodiments were described above in terms of pulse oximetry and oxygen saturation measurements, one of ordinary skill in the art will recognize that an alarm processor as disclosed herein is also applicable to the measurement and monitoring of other blood constituents, for example blood glucose and total hemoglobin concentration to name a few, and other physiological parameters such as blood pressure, pulse rate, respiration rate, and EKG to name a few.

In an embodiment, multiple pattern processors, each including a pattern extractor, pattern memory and pattern comparator, such as described with respect to FIG. 7, above, have as inputs one or more of fast SpO$_2$ measurements, a pulse oximeter plethysmograph and pulse rate measurements. An arrhythmia alarm is generated based upon irregular heartbeat patterns being matched or otherwise detected in one or more combinations of SpO$_2$ measurements, a pulse oximeter plethysmograph and pulse rate measurements.

A physiological trend monitor has been disclosed in detail in connection with various embodiments. These embodiments are disclosed by way of examples only and are not to limit the scope of the claims that follow. One of ordinary skill in the art will appreciate many variations and modifications.

What is claimed is:
1. A physiological trend monitoring method comprising:
transmitting light having multiple wavelengths into a patient tissue site;
generating a sensor signal responsive to the light after attenuation by pulsatile arterial blood flow within the tissue site;
detecting a blood parameter trend according to the sensor signal; and
generating an alarm according to the blood parameter trend.
2. The physiological trend monitoring method according to claim 1 wherein the detecting comprises deriving a curve-fitting blood parameter measurement.

3. The physiological trend monitoring method according to claim 2 further comprising calculating a blood parameter slope from the blood parameter measurement.

4. The physiological trend monitoring method according to claim 3 wherein the alarm is responsive to a negative value of the blood parameter slope.

5. The physiological trend monitoring method according to claim 4 further comprising:
   deriving a smoothed blood parameter measurement;
   and setting a threshold value for the smoothed blood parameter measurement;
   wherein the alarm is responsive to the smoothed blood parameter measurement crossing the threshold value.

6. A physiological trend monitor comprising:
   a sensor signal responsive to multiple wavelengths of light transmitted into a tissue site and detected after attenuation by pulsatile blood flow within the tissue site;
   a processor having an input responsive to the sensor signal and a physiological parameter output;
   a plurality of features extracted from the physiological parameter output, wherein said features comprise statistical characteristics;
   a plurality of criteria applied to the features, wherein said criteria comprise rules corresponding to said statistical characteristics; and
   an alarm output generated when the criteria are satisfied.

7. The physiological trend monitor according to claim 6 further comprising:
   a pattern memory that stores feature values; and
   a comparator that compares the features with the stored feature values;
   the criteria determining a match between the features and the stored feature values so as to trigger the alarm output.

8. The physiological trend monitor according to claim 7 wherein at least one of the features relate to the number of threshold crossings over a specified time period.

9. The physiological trend monitor according to claim 8 wherein at least one of the features relate to a duration of a threshold crossing by the physiological parameter output.

10. The physiological trend monitor according to claim 9 wherein at least one of the features relate to a trend in the physiological parameter and a slope of that trend over a specified time period.

11. A physiological trend monitor comprising:
    a detector responsive to multiple wavelengths of light transmitted into a tissue site after attenuation by pulsatile blood flow within the tissue site so as to generate a sensor signal;
    a processor means for calculating a physiological measurement in response to the sensor signal;
    a pattern extractor means for identifying features of the physiological measurement;
    a pattern memory means for storing a reference pattern; and
    a pattern comparator means for triggering an alarm if the identified features match the reference pattern.

12. The physiological trend monitor according to claim 11 further comprising:
    a threshold input to the pattern extractor, wherein the identified features comprise at least the number of times the physiological measurement crosses the threshold within a predetermined time period.

13. The physiological trend monitor according to claim 12 wherein the identified features comprise at least the duration of each time the physiological measurement crosses the threshold.

14. The physiological trend monitor according to claim 13 wherein the physiological measurement comprises a predictive oxygen saturation measurement.

15. The physiological trend monitor according to claim 14 further comprising a second processor means for calculating an integrator oxygen saturation measurement.

* * * * *

UNITED STATES PATENT AND TRADEMARK OFFICE
CERTIFICATE OF CORRECTION

PATENT NO. : 7,880,606 B2  Page 1 of 1
APPLICATION NO. : 12/070061
DATED : February 1, 2011
INVENTOR(S) : Ammar Al-Ali It is certified that error appears in the above-identified patent and that said Letters Patent is hereby corrected as shown below:

Title Page, item (56);

At the list of references on Page 2, column 2, line 33, please delete "Al-All" and insert therefore, --Al-Ali--.

At column 6, line 13, please delete "$T_1$" and insert therefore, --$\tau_1$--.

At column 6, line 14, please delete "$T_2$, where the value of $T_1$ and $T_2$" and insert therefore, --$\tau_2$, where the value of $\tau_1$ and $\tau_2$--.

At column 6, line 16, please delete "$T_2$" and insert therefore, --$\tau_2$--.

At column 6, line 18, please delete "$T_1=T_2$" and insert therefore, --$T_1=\tau_2$--.

At column 6, line 21, please delete "$T_2=T_2$" and insert therefore, --$T_2=\tau_2$--.

At column 6, line 24, please delete "$T_3=T_2$" and insert therefore, --$T_3=\tau_2$--.

Signed and Sealed this
Twentieth Day of December, 2011

David J. Kappos
*Director of the United States Patent and Trademark Office*

US007880606C1

(12) EX PARTE REEXAMINATION CERTIFICATE (10051st)
United States Patent
Al-Ali

(10) Number: US 7,880,606 C1
(45) Certificate Issued: Feb. 24, 2014

(54) PHYSIOLOGICAL TREND MONITOR

(75) Inventor: Ammar Al-Ali, Tustin, CA (US)

(73) Assignee: Broadwood Partners, L.P., New York, NY (US)

Reexamination Request:
No. 90/012,548, Sep. 13, 2012

Reexamination Certificate for:
Patent No.: 7,880,606
Issued: Feb. 1, 2011
Appl. No.: 12/070,061
Filed: Feb. 12, 2008

Certificate of Correction issued Dec. 20, 2011

Related U.S. Application Data

(63) Continuation of application No. 11/717,591, filed on Mar. 13, 2007, now Pat. No. 7,355,512, which is a continuation of application No. 11/405,815, filed on Apr. 18, 2006, now Pat. No. 7,190,261, which is a continuation of application No. 10/975,860, filed on Oct. 28, 2004, now Pat. No. 7,030,749, which is a continuation of application No. 10/351,735, filed on Jan. 24, 2003, now Pat. No. 6,822,564.

(60) Provisional application No. 60/351,510, filed on Jan. 24, 2002.

(51) Int. Cl.
*G08B 29/00* (2006.01)
*A61B 5/00* (2006.01)

(52) U.S. Cl.
USPC ....... 340/511; 340/539.12; 600/309; 600/323

(58) Field of Classification Search
None
See application file for complete search history.

(56) References Cited

To view the complete listing of prior art documents cited during the proceeding for Reexamination Control Number 90/012,548, please refer to the USPTO's public Patent Application Information Retrieval (PAIR) system under the Display References tab.

*Primary Examiner* — Robert Nasser

(57) ABSTRACT

A physiological trend monitor has a sensor signal responsive to multiple wavelengths of light transmitted into a tissue site. The transmitted light is detected after attenuation by pulsatile blood flow within the tissue site. A processor has an input responsive to the sensor signal and a physiological parameter output. Features are extracted from the physiological parameter output. Criteria are applied to the features. An alarm output is generated when the criteria are satisfied.

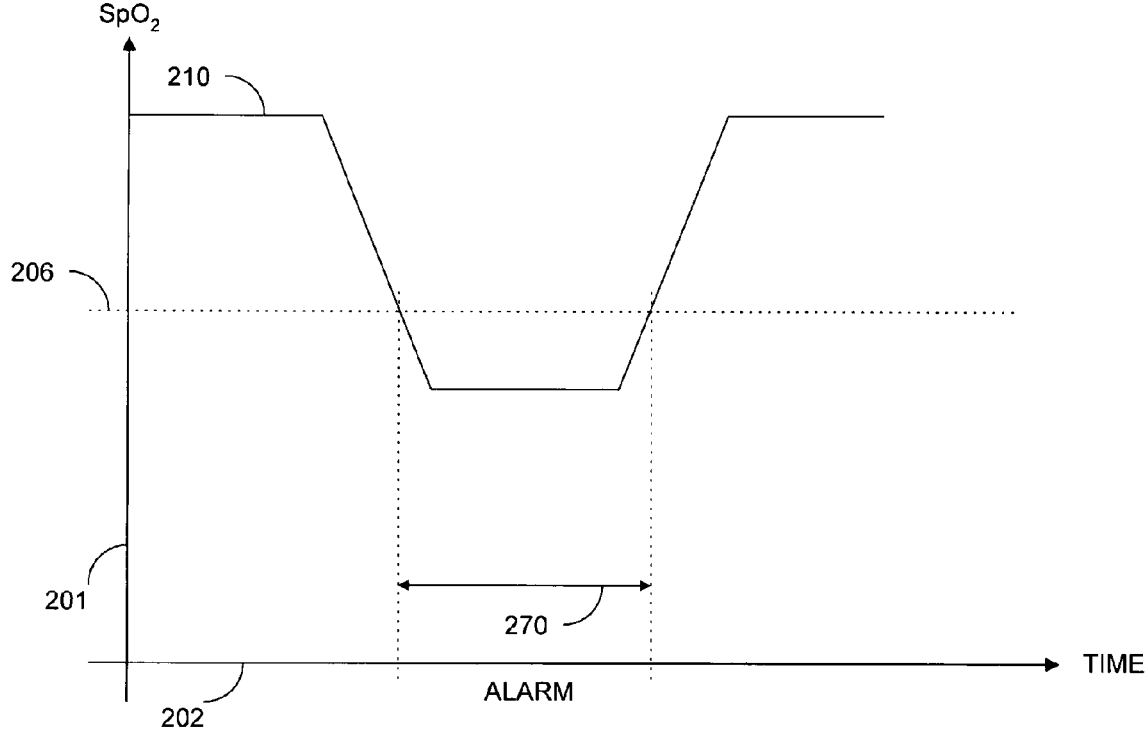

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 3, 5 and 7-10 are cancelled.

Claims 1, 4, 6 and 11 are determined to be patentable as amended.

Claims 2 and 12-15, dependent on an amended claim, are determined to be patentable.

New claims 16-31 are added and determined to be patentable.

1. A physiological trend monitoring method comprising:
   transmitting light having multiple wavelengths into a patient tissue site;
   generating a sensor signal responsive to the light after attenuation by pulsatile arterial blood flow within the tissue site;
   detecting a blood parameter trend according to the sensor signal; [and]
   *electronically deriving a smoothed blood parameter measurement according to the sensor signal;*
   *electronically setting a threshold value for the smoothed blood parameter measurement; and*
   *electronically* generating an *audible* alarm according to *both the smoothed blood parameter measurement crossing the threshold value and a calculated slope of* the blood parameter trend.

4. The physiological trend monitoring method according to claim [3] *1* wherein the alarm is responsive to a negative value of the [blood parameter] *calculated* slope *of the blood parameter trend*.

6. A physiological trend monitor comprising:
   a sensor signal responsive to multiple wavelengths of light transmitted into a tissue site and detected after attenuation by pulsatile blood flow within the tissue site; *and*
   a processor having an input responsive to the sensor signal and a physiological parameter output[;]*, the processor configured to:*
   *extract* a plurality of features [extracted] from the physiological parameter output, wherein said features comprise statistical characteristics, *wherein a first one of the features relates to a trend in the physiological parameter output, and wherein a second one of the features relates to a smoothed value of the physiological parameter output;*
   *apply* a plurality of criteria [applied] to the features, wherein said criteria comprise rules corresponding to said statistical characteristics, *wherein said rules comprise:*
   *a determination of whether the calculated slope of the trend is other than a positive slope, and*
   *a determination of whether the smoothed value of the physiological parameter has crossed a threshold value; and*
   generate an *audible* alarm output [generated] when the criteria together are satisfied.

11. A physiological trend monitor comprising:
    a detector responsive to multiple wavelengths of light transmitted into a tissue site after attenuation by pulsatile blood flow within the tissue site so as to generate a sensor signal;
    a processor means for calculating a physiological measurement in response to the sensor signal, *the processor means further configured to calculate a smoothed physiological parameter measurement;*
    *a threshold detector configured to trigger an audible alarm responsive to the smoothed physiological parameter measurement crossing a threshold value;*
    a pattern extractor means for identifying features of the physiological measurement;
    a pattern memory means for storing a reference pattern; and
    a pattern comparator means for triggering [an] *the audible* alarm if the identified features match the reference pattern, *wherein the pattern comparator means are further configured to trigger the audible alarm even if the smoothed physiological measurement has not yet crossed the threshold value.*

16. *The physiological trend monitoring method according to claim 1 wherein said generating said audible alarm comprises generating said audible alarm responsive to a zero value of the calculated slope of the blood parameter trend.*

17. *The physiological trend monitoring method according to claim 1, comprising providing a visual alarm for output to a display responsive to the calculated slope of the blood parameter trend.*

18. *The physiological trend monitoring method according to claim 1, wherein the blood parameter trend tracks changes in a blood parameter.*

19. *The physiological trend monitoring method according to claim 1, further comprising electronically suppressing the audible alarm responsive to a positive value of the calculated slope.*

20. *The physiological trend monitor according to claim 6, wherein at least one of the rules comprises a determination of whether the calculated slope is zero, and wherein the alarm output is generated when the calculated slope is zero.*

21. *The physiological trend monitor according to claim 6, wherein at least one of the rules comprises a determination of whether the calculated slope is negative, and wherein the alarm output is generated when the calculated slope is negative.*

22. *The physiological trend monitor according to claim 6, wherein the processor is further configured to suppress the audible alarm responsive to a positive value of the calculated slope.*

23. *The physiological trend monitor according to claim 11, wherein the reference pattern corresponds to irregular oxygen saturation.*

24. *A physiological trend monitoring method comprising:*
    *transmitting light having multiple wavelengths into a patient tissue site;*
    *generating a sensor signal responsive to the light after attenuation by pulsatile arterial blood flow within the tissue site;*
    *electronically detecting a blood parameter and a blood parameter trend according to the sensor signal; and*
    *electronically generating an audible alarm according to the blood parameter trend, said audible alarm initially suppressed from said blood parameter being below a threshold value and subsequently suppressed from said* blood parameter being below said threshold value, said suppression responsive to a calculated slope of the blood parameter trend.

25. The physiological trend monitoring method according to claim 24, wherein said generating said alarm comprises generating said alarm when said calculated slope is a negative value.

26. The physiological trend monitoring method according to claim 24, wherein said generating said alarm comprises generating said alarm when said calculated slope is a non-positive value.

27. The physiological trend monitoring method according to claim 24, wherein said generating said alarm comprises generating said alarm when said calculated slope is zero.

28. The physiological trend monitoring method according to claim 24, wherein said audible alarm is suppressed when the calculated slope is any positive value.

29. The physiological trend monitoring method according to claim 24, wherein said audible alarm is suppressed upon electronic determination that a monitored patient is recovering.

30. The physiological trend monitoring method according to claim 24, wherein said blood parameter comprises oxygen saturation, wherein said generating said alarm comprises generating said alarm upon a combined condition, said combined condition being when said calculated slope is a nonpositive value and said oxygen saturation is below a threshold.

31. The physiological trend monitoring method according to claim 30, wherein said oxygen saturation comprises a smoothed value of said oxygen saturation.

\* \* \* \* \*